United States Patent [19]

Lancaster et al.

[11] Patent Number: 4,891,382

[45] Date of Patent: Jan. 2, 1990

[54] METHOD OF PREVENTING PANCREATITIS UTILIZING 2-AMINO-CYCLOALIPHATIC AMIDES

[75] Inventors: Cleo Lancaster; Andre Robert, both of Kalamazoo, Mich.

[73] Assignee: The Upjohn Company, Kalamazoo, Mich.

[21] Appl. No.: 184,647

[22] Filed: Apr. 22, 1988

[51] Int. Cl.[4] .................... A61K 31/40; A61K 31/495
[52] U.S. Cl. ..................................... 514/429; 514/255
[58] Field of Search ............... 514/824, 825, 429, 671, 514/255

[56] References Cited

U.S. PATENT DOCUMENTS 4,145,435  3/1979  Szmuszkovicz ..................... 514/429
4,522,827  6/1985  Marlettini et al. .................. 514/671

Primary Examiner—Douglas W. Robinson
Assistant Examiner—Zohieh A. Fay
Attorney, Agent, or Firm—Sidney B. Williams, Jr.

[57] ABSTRACT

A method for the prevention of pancreatitis utilizing cis- and trans-N-(3-aminocycloaliphatic)-2-arylacetamide derivative compounds of the formula

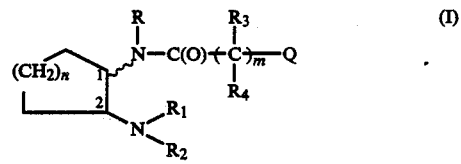

e.g., N-[2-(n',N'-dimethylamino)cyclohexyl]-N-methyl-2-(4-bromophenyl)acetamide and trans-N-methyl-N-[2-(1-pyrrolidinyl)cyclohexyl]acetamide, 2-(3,4-dichlorophenyl) and their pharmaceutically acceptable salts.

10 Claims, No Drawings

METHOD OF PREVENTING PANCREATITIS UTILIZING 2-AMINO-CYCLOALIPHATIC AMIDES

BACKGROUND OF THE INVENTION

This invention relates to a method for the prevention and treatment of inflammatory diseases of the pancreas utilizing cis- and trans-N-(3-aminocycloaliphatic)-2-arylacetamides.

Acute pancreatitis is a severe disease with a prevalence of 30,000 cases per year in the U.S. and for which no specific treatment exists. Mortality rate from hemorrhagic pancreatitis exceeds 50%.

INFORMATION DISCLOSURE

To applicants' knowledge, no disclosure of cis- and trans-N-(2-aminocycloaliphatics and their pharmaceutically acceptable salts has been made for prevention or treatment of pancreatic inflammatory disease. However, their use as analgesics are disclosed in U.S. Pat. No. 4,145,435.

Jackson, A. and Cooper, S. J., "Effects of Kappa Opiate Agonist on Palatable Food Consumption in Non-deprived Rats, With and Without Food Preloads", *Brain Res. Bull.*, 15: 391–396 (1985).

Jackson, A. and Cooper, S. J., "The Involvement of the Kappa Opiate Receptor in the Control of Food Intake in the Rat", *Neuropharmaceology*, 25: 653–654 (1986).

Louie, D. S., Chen, H. T., and Owyang, C., "Inhibition of Exocrine Pancreatic Secretion by Opiates is Mediated by Suppression of Cholinergic Tranmission: Characterization of Receptor Subtypes", *Can. J. Physiol. Pharmacol.*, July Suppl., 12 (9186).

Chang, R. S. L., Lotti, V. J., Chen, B. T. and Keegan, M. E., *Tifluadom, a K-opiate Agonist, Acts as a Peripheral Cholecystokinin Receptor Antagonist*", *Neuoscience Letters*, 72: 211–214 (1986).

Konturek et al reported that enkephalin inhibits gastric and pancreatic secretions, in dogs, effects that were reversed by naloxone. The anti-secretory action of naloxone supports the concept of a stimulatory action for endogenous opiates on gastric secretion. It was suggested that the action of opiates on gastric oxynitic glands (secreting acid) is mediated by opiate receptors and that endogenous opiates may be involved in the endogenous stimulation of gastric secretion. Inhibition of gastric secretion by enkephalin contradicts this hypothesis. Since trans-N-[2-(1-pyrrolidinyl)cyclohexyl]-N-methyl-2-(3,4-dichlorophenyl)-acetamide hydrochloride, a specific kappa receptor agonist, stimulated basal secretion, the kappa opioid receptor on the oxyntic glands may modulate opioid-induced gastric secretion. These results support Konturek's hypothesis.

SUMMARY OF THE INVENTION

This invention relates to the use of 2-aminocycloaliphatic amide compounds for the prevention of pancreatitis.

The present invention particularly provides:

A method for the prevention and treatment of pancreatitis which comprises administering to a patient a compound of formula I wherein the ~ at the 1-position of the cycloaliphatic ring denotes cis- or trans-stereoconfiguration of the 1-position substituent with respect to the substituent in 2-position of the same cycloaliphatic ring;

R is $C_1$ to $C_3$-alkyl;

$R_1$ and $R_2$, taken separately, are $C_1$ to $C_3$-alkyl, or when $R_1$ is $C_1$ to $C_3$alkyl, $R_2$ is $C_1$ to $C_6$-alkyl, $-CH_2CH_2CF_3$, $C_3$ to $C_6$-(allylic)alkenyl, $C_2$ to $C_5$-hydroxyalkyl, $C_3$ to $C_6$-cycloalkyl, $C_3$ to $C_6$-cycloalkyl, $C_3$ to $C_4$-cycloalkylmethyl, phenyl-$C_1$ to $C_3$-alkyl, or $R_1$ and $R_2$ taken together with the nitrogen to which they are bonded complete a saturated, monocyclic, mononitrogen heterocyclic ring containing only carbon and nitrogen ring atoms and containing from 3 to 4 carbon atoms; said saturated monocyclic nitrogen heterocyclic rings having 3 to 4 ring carbon atoms permissively being substituted in the 3-position of the ring with hydroxy, $C_1$ to $C_3$-alkyloxy, or $C_1$ to $C_3$-alkanoyloxy; or N-piperazinyl ring, permissively substituted on the N'-nitrogen with a $C_1$ to $C_3$-alkyl;

$R_3$ is hydrogen or methyl;

$R_4$ is hydrogen or methyl, $R_3$ and $R_4$ can be taken together with the carbon to which they are bonded to complete a cyclopropylene ring;

m is 1 to 4 and is 2 to 4 only when $R_3$ and $R_4$ are both hydrogen;

n is 2 to 4; and

Q is 1-naphthyl, 2-naphthyl or wherein each of X, Y and Z is hydrogen, a halogen having an atomic number of from 9 to 35, trifluoromethyl, $C_2$ to $C_3$-alkyl, $C_1$ to $C_3$-alkyloxy, azido or phenyl, and at least one Z, Y and Z is a substituent other than hydrogen, and when one of X, Y and Z is azido, phenyl, $C_1$ to $C_3$-moieties are hydrogen; and the pharmaceutically acceptable salts thereof.

A preferred method involves the use of compounds of formula I wherein the substituent at the 1-position of he cycloaliphatic ring is in the trans-steroconfiguration with respect to the substituent in the 2-position of the same cycloaliphatic ring.

With respect to the method described above, pancreatic inflammatory diseases include specifically hemorraghic, acute and chronic pancreatitis, chronic pancreas inflammation caused by infections, parasites, bilary obstruction, obstruction of the pancreatic ducts, alcoholism, primary hyperparathyroidism, renal transplantation, hyperlipemia, pregnancy, immunologic processes, drugs, scorpion venom, hypothermia, alpha 1-antitrypsin deficiency and idiopathic pancreatitis.

A further aspect of the present invention resides in the selection of patients for the present method who exhibit a high susceptibility to the acquisition of pancreatic inflammatory diseases. In accordance with the invention, patients who will benefit from these anti-pancreatitis compounds will fall into several classes.

First, patients with pancreatitis of an unknown cause (idiopathic pancreatitis). Further, patients for whom treatment by the present method is indicated include persons exhibiting chronic and excessive ethanol consumption. In particular, the use of the present method by persons diagnosed as alcoholics. Especially suitable candidates for the present method are those alcoholics with a history of recurrent or persistent pancreatitis. Further included as suitable subjects for treatment by the present method are humans stung by the scorpion *Tityrus trinitatis*. The scorpion's venom can induce pancreatitis.

Suitable subjects for treatment by the present method are humans who develop pancreas inflammatory disease while being treated with glucocorticosteroids (after organ transplantation) azathioprine, thiazides and estrogens or who suffer an accidental overdose of these drugs.

Finally, the present invention is employed in subjects exhibiting pancreatitis after a recent exposure to pathogens such as coxsackie B virus, *Mycoplasma pneumonrae*, viral hepatitis, bacterial infections of the bilary tract, salmonellosis and streptococcal infections, and pancreatitic duct obstruction by *Asceris lumbricoides*.

EMBODIMENTS OF THE INVENTION

Methods for the preparation of pharmaceutical compositions containing cis- and trans-N-(2-aminocycloaliphatic)-2-arylacetamides, their pharmaceutically acceptable salts and their use as analgesics are described in U.S. Pat. No. 4,145,435, the essential matter thereof being incorporated by reference.

The present invention requires administration of a dose of the compound effective to treat or prevent the development of the pancreatic inflammatory disease. Thus, the dose required in accordance with the present invention is sufficiently great so as to permit the prevention and/or healing effect. The compound can be administered in oral, intramuscular, or intravenous formulations.

The dosage regimen for the claimed compounds in accord with this invention will depend on a variety of factors, including the type, age, weight, sex and medical condition of the mammal, nature and severity of the pancreatic inflammatory disease and the particular compound to be administered. It is within the skill of the attending physician or veterinarian to determine the patient's susceptibility to the gastric inflammatory disease, and to prescribe an effective amount of the compound to prevent it. In doing that, the physician or veterinarian would by one method start at a relatively low dose of the compound, for example, about 0.1 gm. three times a day to about 1 gm. three times a day, and observe the response of the patient as shown by clinical improvement and/or lowering of serum amylase for a few days. The dose is then adjusted downward or upward until the maximum effective dose is found. Once the minimum effective dose of the particular compound is determined for a particular subject, it is advantageous to provide the subject with the dosage schedule which will provide a substantially uniform level of the compound. For example, the dosage needed for prevention in humans is between about 0.025 gm. and about 1 gm. three times a day although it may be necessary to occasionally exceed those doses when the susceptibility to the pancreatic inflammatory disease is especially severe. The dosage needed for treatment of humans is between about 0.1 gm and 6.0 gm three times a day.

DESCRIPTION OF THE PREFERRED EMBODIMENTS

The efficacy of the compounds of the present invention prevented pancreatitis as is seen by the example below.

EXAMPLE

Sprague-Dawly rats of an average body weight of 210 g. were used. Caerulein (Sigma Co., St. Louis, MO) was infused subcutaneously at a dose of 8 $\mu$l./kg. per hour at a rate of one ml. per hour. Food and water were removed at the time the infusion started. Five hours after the beginning of caerulein infusion, the animals were anesthesized with ether, the abdominal aorta was exposed, and blood was drawn into a 3 ml. plastic syringe [containing 0.2 ml. of heparin (200 IU)] to the 3 ml. mark. Plasma amylase was determined. The pancreas was weighed and fixed in 10% buffered formalin for histological examination.

In caerulein plus saline-treated rats, the pancreas weight increased by 75% and the plasma amylase increased seven-fold. Histologically, the pancreatic lesions were characterized by edema, formation of cytoplasmic vacuoles in acinar cells, leukocytic infiltration and necrosis (the latter identified by the presence of pyknotic nuclei in acinar cells).

The increase in pancreas weight and plasma amylase caused by caerulein was reduced in a dose-related manner by trans-N-[2-(1-pyrrolidinyl)cyclohexyl]-N-methyl-2-(3,4-dichlorophenyl)-acetamide hydrochloride. A dose of 15 mg./kg. orally or subcutaneously completely prevented the caerulein-induced rise in pancreas weight, whereas the dose preventing the rise of plasma amylase was 50 mg./kg. The $ED_{50}$ for plasma amylase after oral administration was 15 mg./kg.

STRUCTURES

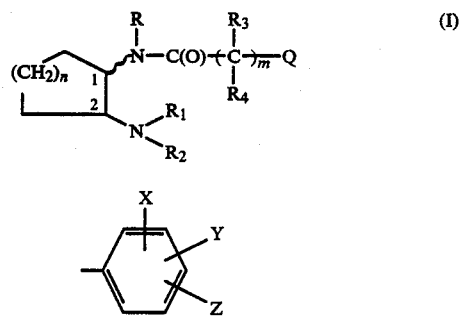

We claim:
1. A method for the prevention of pancreatitis in a patient susceptible thereto which comprises administering to a patient a preventative amount of a compound of the formula

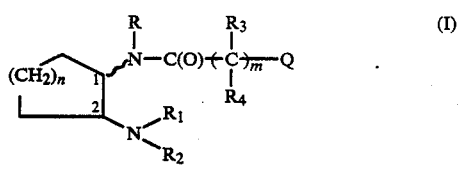

wherein
the ~ at the 1-position of the cycloaliphatic ring denotes trans-stereoconfiguration of the 1-position substituent with respect to the substituent in position 2 of the same cycloaliphatic ring;
R is $C_1$ to $C_3$-alkyl;
$R_1$ and $R_2$, taken separately, are $C_1$ to $C_3$-alkyl, or when $R_1$ is $C_1$ to $C_3$-alkyl, $R_2$ is $C_1$ to $C_6$-alkyl, -$CH_2CF_3$, $C_3$ to $C_6$-(allylic)-alkenyl, $C_2$ to $C_5$-hydroxyalkyl, $C_3$ to $C_6$-cycloalkyl, $C_3$ to $C_6$-cycloalkyl, $C_3$ to $C_4$-cycloalkylmethyl, phenyl-$C_1$ to $C_3$-alkyl, or $R_1$ and $R_2$ taken together with the nitrogen to which they are bonded complete a saturated, monocyclic, mononitrogen heterocyclic ring containing only carbon and nitrogen ring atoms and containing from 3 to 4 carbon atoms; said saturated monocyclic nitrogen heterocyclic rings having 3 to 4 ring carbon atoms permissively being substituted in the 3-position of the ring with hydroxy, $C_1$ to $C_3$-alkyloxy, or $C_1$ to $C_3$-alkanoyloxy; or N-piperazinyl ring, permissively substituted on the N'-nitrogen with a $C_1$ to $C_3$-alkyl;

$R_3$ is hydrogen or methyl;

$R_4$ is hydrogen or methyl, $R_3$ and $R_4$ can be taken together with the carbon to which they are bonded to complete a cyclopropylene ring;

m is 1 to 4 and is 2 to 4 only when $R_3$ and $R_4$ are both hydrogen;

n is 2 to 4; and

Q is 1-naphthyl, 2-naphthyl or

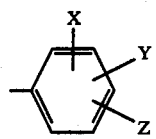

wherein each of X, Y and Z is hydrogen, a halogen having an atomic number of from 9 to 35, trifluoromethyl, $C_2$ to $C_3$-alkyl, $C_1$ to $C_3$-alkyloxy, azido or phenyl, and at least one of X, Y and Z is a substituent other than hydrogen, and when one of X, Y and Z is azido, phenyl $C_1$ to $C_3$-moieties are hydrogen, or the pharmaceutically acceptable salts thereof.

2. A method according to claim 1 wherein

R is $C_1$ to $C_3$-alkyl;

$R_1$ and $R_2$ are each $C_1$ to $C_3$-alkyl;

$R_3$ and $R_4$ are each hydrogen;

n is 2;

m is 1;

Q is

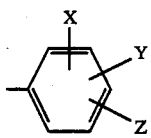

wherein at least one of X, Y and Z is a halogen having an atomic number of from 9 to 35, or pharmaceutically acceptable salts thereof.

3. A method according to claim 2 wherein the compound is in the trans-configuration wherein R is methyl;

$R_1$ and $R_2$ are each methyl;

$R_3$ and $R_4$ are each hydrogen;

n is 2;

m is 1;

Q is

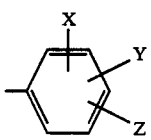

wherein X is bromo in the 4-position and Y and Z are hydrogen, or the pharmaceutically acceptable salts thereof.

4. A method according to claim 2 wherein the compound is in the trans-configuration wherein R is methyl;

$R_1$ and $R_2$ are each methyl;

$R_3$ and $R_4$ are each hydrogen;

n is 2;

m is 1;

Q is

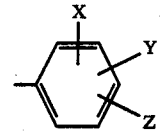

wherein X and Y are each chloro in the 3- and 4-positions and Z is hydrogen, or the pharmaceutically acceptable salts thereof.

5. A method according to claim 1 wherein

R is $C_1$ to $C_3$-alkyl;

$R_1$ and $R_2$ are taken together with the nitrogen atom to which they are bonded to complete a saturated monocyclic mononitrogen heterocyclic ring containing from 3 to 4 ring carbon atoms;

$R_3$ and $R_4$ are each hydrogen;

n is 2;

m is 1, and

Q is

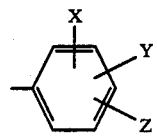

wherein at least one of X, Y and Z is a halogen having an atomic number of from 9 to 35, or azido, or pharmaceutically acceptable salts thereof.

6. A method according to claim 5 wherein the compound is in the trans-configuration wherein R is methyl;

$R_1$ and $R_2$ are taken together with the nitrogen to which they are bonded to complete a pyrrolidine ring;

$R_3$ and $R_4$ are each hydrogen;

n is 2;

m is 1; and

Q is

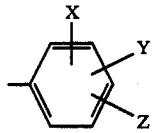

wherein X is bromo in the 4-position and Y and Z are hydrogen, or the pharmaceutically acceptable salts thereof.

7. A method according to claim 5 wherein the compound is in the trans-configuration wherein R is methyl;

$R_1$ and $R_2$ are taken together with the nitrogen to which they are bonded to complete a pyrrolidine ring;

$R_3$ and $R_4$ are each hydrogen;

n is 2;

m is 1; and
Q is

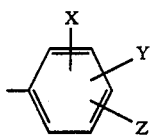

wherein X and Y are chloro in the 3 and 4-positions and Z is hydrogen or the pharmaceutically acceptable salts thereof.

8. A method according to claim 7 wherein the compound is trans-N-[2-(1-pyrrolidinyl)cyclohexyl]-N-methyl-2-(3,4-dichlorophenyl)-acetamide hydrochloride.

9. A method for the treatment of pancreatitis in a patient in need thereof, which comprises administering to a patient a therapeutically effective amount of a compound of the formula

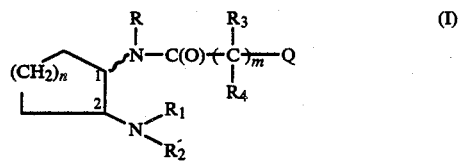

(I)

wherein
the ~ at the 1-position of the cycloaliphatic ring denotes trans-stereoconfiguration of the 1-position substituent with respect to the substituent in position 2 of the same cycloaliphatic ring;
R is $C_1$ to $C_3$-alkyl;
$R_1$ and $R_2$, taken separately, are $C_1$ to $C_3$-alkyl, or when $R_1$ is $C_1$ to $C_3$-alkyl, $R_2$ is $C_1$ to $C_6$-alkyl, -$CH_2CF_3$, $C_3$ to $C_6$-(allylic)alkenyl, $C_2$ to $C_5$-hydroxyalkyl, $C_3$ to $C_6$-cycloalkyl, $C_3$ to $C_6$-cycloalkyl, $C_3$ to $C_4$-cycloalkylmethyl, phenyl-$C_1$ to $C_3$-alkyl, or $R_1$ and $R_2$ taken together with the nitrogen to which they are bonded complete a saturated, monocyclic, mononitrogen heterocyclic ring containing only carbon and nitrogen ring atoms and containing from 3 to 4 carbon atoms; said saturated monocyclic nitrogen heterocyclic rings having 3 to 4 ring carbon atoms permissively being substituted in the 3-position of the ring with hydroxy, $C_1$ to $C_3$-alkyloxy, or $C_1$ to $C_3$-alkanoyloxy; or N-piperazinyl ring; permissively substituted on the N'-nitrogen with a $C_1$ to $C_3$-alkyl;
$R_3$ is hydrogen or methyl;
$R_4$ is hydrogen or methyl, $R_3$ and $R_4$ can be taken together with the carbon to which they are bonded to complete a cyclopropylene ring;
m is 1 to 4 and is 2 to 4 only when $R_3$ and $R_4$ are both hydrogen;
n is 2 to 4; and
Q is 1-naphthyl, 2-naphthyl or

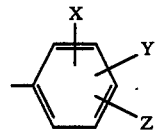

wherein each of X, Y and Z is hydrogen, a halogen having an atomic number of from 9 to 35, trifluoromethyl, $C_2$ to $C_3$-alkyl, $C_1$ to $C_3$-alkyloxy, azido or phenyl, and at least one of X, Y and Z is a substituent other than hydrogen, and when one of X, Y and Z is azido, phenyl, $C_1$ to $C_3$-moieties are hydrogen, or the pharmaceutically acceptable salts thereof.

10. A method according to claim 9 wherein the compound is trans-N-[2-(1-pyrrolidinyl)cyclohexyl]-N-methyl-2-(3,4-dichlorophenyl)acetamide hydrochloride.

* * * * *